(12) United States Patent
Doerr et al.

(10) Patent No.: US 8,942,820 B2
(45) Date of Patent: Jan. 27, 2015

(54) IMPLANTABLE ELECTRODE LEAD

(71) Applicant: Biotronik SE & Co. KG, Berlin (DE)

(72) Inventors: Thomas Doerr, Berlin (DE); Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 167 days.

(21) Appl. No.: 13/677,310

(22) Filed: Nov. 15, 2012

(65) Prior Publication Data

US 2013/0150932 A1 Jun. 13, 2013

Related U.S. Application Data

(60) Provisional application No. 61/568,182, filed on Dec. 8, 2011.

(51) Int. Cl.
- *A61N 1/00* (2006.01)
- *A61N 1/05* (2006.01)
- *A61N 1/375* (2006.01)
- *A61N 1/08* (2006.01)

(52) U.S. Cl.
CPC ...... *A61N 1/05* (2013.01); *A61N 1/375* (2013.01); *A61N 1/056* (2013.01); *A61N 2001/086* (2013.01)
USPC ........................ 607/116; 607/117; 607/126

(58) Field of Classification Search
CPC ............... A61N 2001/086; A61N 2001/86; A61N 1/375; A61N 1/05; A61N 1/056
USPC ......................................... 607/116–119, 126
See application file for complete search history.

(56) References Cited

U.S. PATENT DOCUMENTS

| | | | |
|---|---|---|---|
| 8,498,721 B2 * | 7/2013 | Scheiner et al. | 607/125 |
| 2008/0161886 A1 | 7/2008 | Stevenson et al. | |
| 2011/0087299 A1 | 4/2011 | Ameri | |
| 2011/0208280 A1 * | 8/2011 | Li et al. | 607/115 |
| 2011/0270362 A1 | 11/2011 | Goedeke et al. | |

OTHER PUBLICATIONS

European Search Report dated Apr. 16, 2013, 6 pages.

* cited by examiner

*Primary Examiner* — Michael Kahelin
*Assistant Examiner* — Mallika D Fairchild
(74) *Attorney, Agent, or Firm* — ARC IP Law, PC; Joseph J. Mayo

(57) ABSTRACT

An implantable electrode lead comprising an electric supply lead. The electric supply lead is designed to assume, after implantation of the electrode lead in a deformable supply lead section, a shape that is changed such that it induces higher inductance in the deformable supply lead section after deformation than before deformation, wherein the inductance is at least 0.1 μH. The implantable electrode lead can also comprise an outer sleeve within which the supply lead is disposed. The electric supply lead is designed to assume, after implantation of the electrode lead in a deformable supply lead section, a shape that has changed compared to the original shape thereof. The supply lead is also designed and disposed inside the sleeve such that the supply lead, in the deformable supply lead section thereof, is deformable relative to the outer sleeve and inside the outer sleeve.

15 Claims, 4 Drawing Sheets

IMPLANTABLE ELECTRODE LEAD

This application claims the benefit of U.S. Provisional Patent Application 61/568,182 filed on 8 Dec. 2011, the specification of which is hereby incorporated herein by reference.

BACKGROUND OF THE INVENTION

1. Field of the Invention

At least one embodiment of the invention relates to an implantable elongated electrode lead.

2. Description of the Related Art

Electrode leads of are connected, for example, to implantable cardiac stimulators such as cardiac pacemakers, cardioverters, defibrillators or the like, and may also serve as mapping catheters for diagnosis or neurostimulation.

Such electrode leads have the disadvantage that the electric lead thereof can heat up in a nuclear resonance tomograph because the alternating magnetic fields in the nuclear resonance tomograph induce notable electric currents in the electric conductor. For this reason, patients with cardiac pacemakers typically cannot be examined in a nuclear resonance tomograph, or only to a limited extent.

Typically, at least one stimulation electrode lead is connected to implantable cardiac pacemakers or defibrillators, which comprise a standardized electric connector on the proximal end thereof intended for connection to the cardiac pacemaker or defibrillator, and comprise one or more electrode poles on the distal end thereof intended for placement in the heart. Such an electrode pole is used to output electrical pulses, e.g. to the tissue (myocardium) of the heart, or to sense electric fields in order to allow sensing of an activity, such as cardiac activity, within the scope of so-called sensing.

For these purposes, electrode poles typically form electrically conductive surface sections of an electrode lead. Electrode poles are typically provided as ring electrodes in the form of a ring around the electrode lead or in the form of a tip electrode on the distal end of the electrode lead.

The electrode poles are connected in an electrically conductive manner by way of one or more electric supply leads to contacts of the electric connector of the electrode lead at the proximal end thereof. One or more electric supply leads which electrically connect one or more of the electrode poles to one or more of the contacts therefore extend between the contacts of the electric connector of the electrode leads at the proximal end thereof and the electrode poles at the distal end of the electrode lead.

Such supply leads contain electric leads required for the functions of the particular electrode lead and are therefore exposed to the risk that electric currents can be induced therein by external alternating magnetic fields, which can result, for example, in unwanted heating of the supply leads or the electrode poles connected thereto, or which can result in the output of corresponding currents by way of the electrode poles to surrounding tissue and, therefore, in heating of the surrounding tissue.

BRIEF SUMMARY OF THE INVENTION

At least one embodiment of the invention forms an electrode lead which develops less heat than conventional electrode leads in an MRT environment.

According to one or more embodiments of the invention, this feature is achieved by an implantable electrode lead comprising an electrode body, at least one electrode pole connected to the electrode body, a connector and an electric supply lead which is electrically connected to the electrode pole and extends from the electrode pole to the connector at a proximal end of the electrode lead. The electric supply lead is designed to assume, after implantation of the electrode lead in a deformable supply lead section, a shape that is changed or in other words altered, with respect to its normal shape, for example a typical straight line, such that it induces higher inductance in the deformable supply lead section after deformation than before deformation, wherein the inductance is at least 0.1 µH.

According to one or more embodiments of the invention, this feature is also achieved by an implantable electrode lead comprising an electrode body, at least one electrode pole connected to the electrode body, a connector and an electric supply lead which is electrically connected to the electrode pole and extends from the electrode pole to the connector at a proximal end of the electrode lead, wherein the implantable electrode lead comprises an outer sleeve within which the supply lead is disposed. The electric supply lead is designed to assume, after implantation of the electrode lead in a deformable supply lead section, a shape that has altered compared to the original shape thereof. In addition, the supply lead is designed and disposed inside the sleeve such that the supply lead, in the deformable supply lead section thereof, is deformable relative to the outer sleeve and inside the outer sleeve.

The sleeve therefore does not assume the shape of the supply lead section when the latter assumes the altered shape thereof.

In both cases, the intended effect of reducing the heat development of these electrodes is based on the detuning of the antenna properties of the electrode lead, which are resonant for the MRT fields, either by way of a variation of length or geometry and/or by adding an inductor.

In the second case mentioned above, the sleeve is preferably expandable in the region of the deformable supply lead section, and the deformable supply lead section and sleeve are designed such that the sleeve expands radially upon deformation of the deformable supply lead section.

In both cases, an MRT-compatible electrode lead results which, after implantation, assumes a coiled shaped, either entirely or in part, and is therefore a poorly tuned antenna for the MRT-HF fields, thereby reducing the MRT-induced development of heat.

Highly diverse design modifications and the integration of electronic components in electrode leads have been known in order to reduce the MRT-induced development of heat. However, many of the above-mentioned solutions for reducing the MRT-induced development of heat in electrode leads require additional structural features which make the overall design of the electrode lead substantially more complex and add joints, and therefore the reliability of these electrode leads will likely diminish relative to conventional electrode leads.

According to one or more embodiments, the altered shape of the deformable supply lead section after implantation of the electrode lead is a helix. This is suitable for providing the deformable supply lead section with a desired inductance and can also serve to fix the electrode lead after implantation in that the supply lead itself as well as the outer shape of the electrode lead including the external sleeve assume a helical shape in the region of the deformable supply lead section, which rests against the wall of a blood vessel, for example.

The helix preferably comprises at least 15 turns, in particular more than 30 turns. The individual turns of the helix are preferably separated from one another. The altered shape preferably induces an inductance of more than 1 µH.

The altered shape is preferably pre-impressed upon the supply lead. To this end, the electrode lead can be made of a memory metal in such a way that it assumes the altered shape after a trigger temperature has been exceeded. Alternatively or in addition thereto, the electrode lead can be preformed and, upon implantation, can be elastically preloaded using a stiffer, removable insertion aid, and so the supply lead assumes the altered shape after removal of the insertion aid on the preload. The insertion aid is preferably a sleeve catheter or a stylet.

To achieve a pre-impressed shape, it can be provided in the case of a supply lead comprising an electric lead that at least one of the electric leads is enclosed by a jacket, which has been pre-impressed with the altered shape of the supply lead, in the region of the deformable supply lead section. The jacket is preferably formed of a memory material. In addition, it is preferable for the jacket to be formed of insulating plastic.

After deformation, the deformable supply lead section preferably has a diameter of more than 8 mm or, if possible, more than 10 mm. This increases the inductance of the supply lead section.

The deformable supply lead section is preferably provided in the vicinity of a distal end of the electrode lead, although it can also be located on a proximal end of the electrode lead, or in the center thereof. Preferably only one deformable supply lead section is provided, although a plurality thereof can also be provided.

The feature of the invention is therefore achieved with an electrode or sensor lead which can be implanted temporarily or permanently and comprises at least one electric supply lead which is designed such that one or more parts of the electric supply lead or the entire electric supply lead are oriented in a coiled or curled shape after implantation.

To ensure easy explantation of the electrode lead, the deformation is reversible and can be undone, at least temporarily, by inserting a rigid stylet or the like, for example.

BRIEF DESCRIPTION OF THE DRAWINGS

The invention is explained in greater detail with reference to an embodiment and the figures. They show, in.

DETAILED DESCRIPTION OF THE INVENTION

Figure 1:
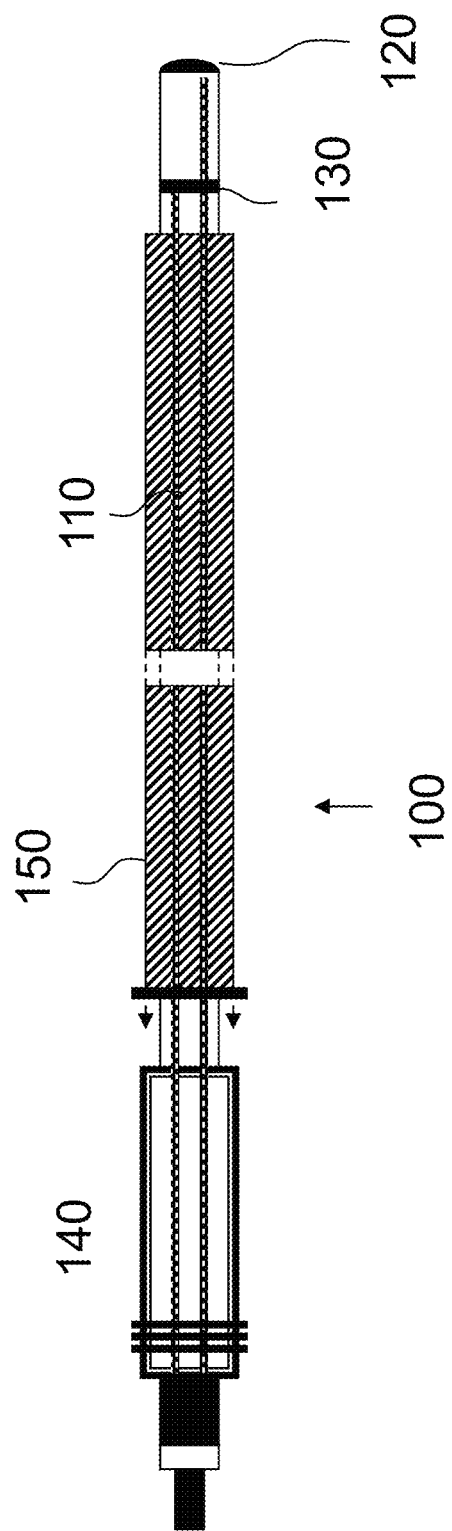
FIG. 1 an electrode lead according to an embodiment of the invention, before implantation.

FIG. 1 shows an electrode lead 100 according to the invention, before implantation. The electrode lead 100 comprises an insulated supply lead 110 or jacket, a bipolar electrode pole (tip: 120, ring 130) and a corresponding connector or connecting plug 140 and an insertion aid 150 to be used temporarily, in order to create an elongated shape upon implantation. In the example shown, this insertion aid 150 is designed as an introducer sheath or tube over the electrode lead. Alternatively, however, a rigid stylet or a mandrel can be used.

Figure 2:
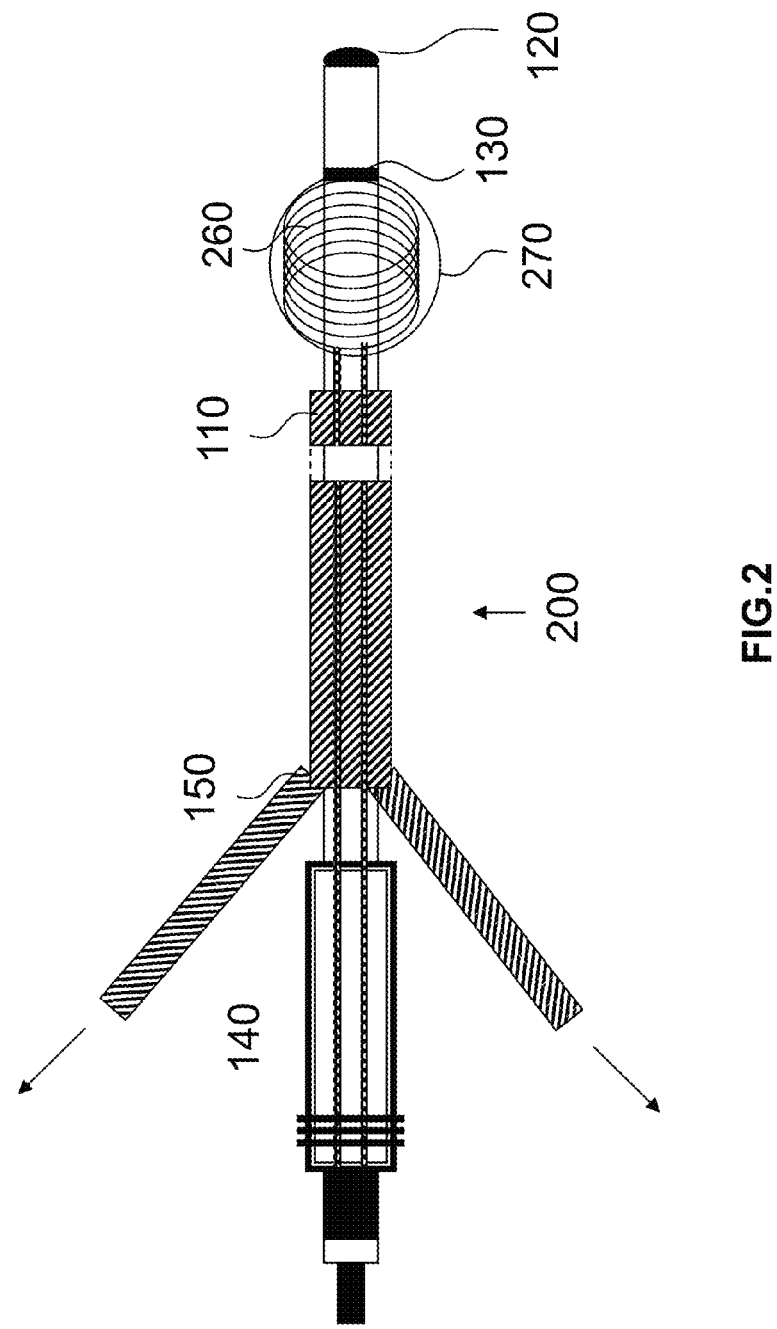
FIG. 2 the electrode lead in FIG. 1, after implantation.
Figure 3:
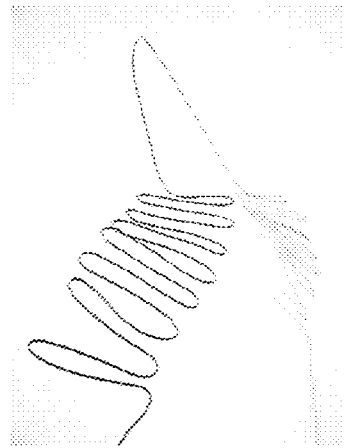
FIGS. 3 to 12 further examples of a supply lead section having an altered shape.
Figure 4:
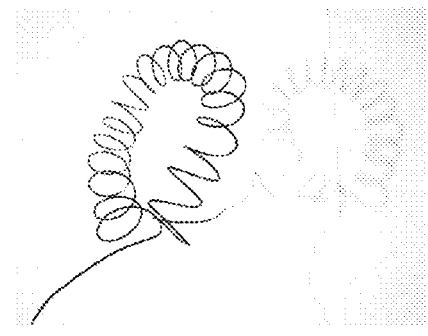
Figure 5A:
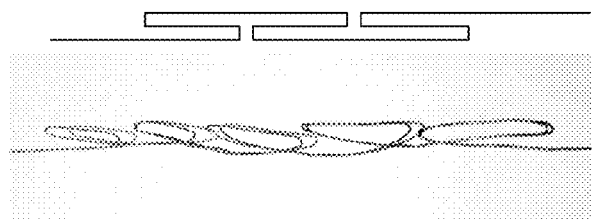
Figure 5B:
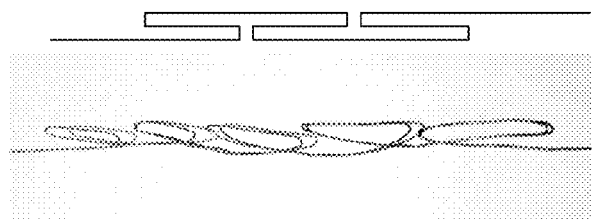
Figure 6:
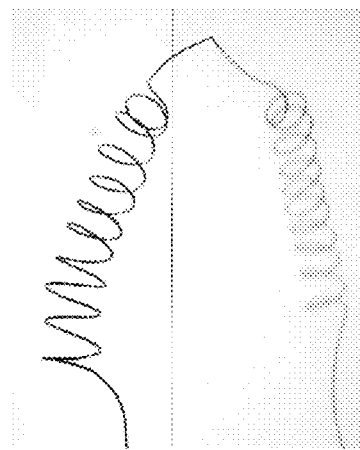
Figure 7:
Figure 10:
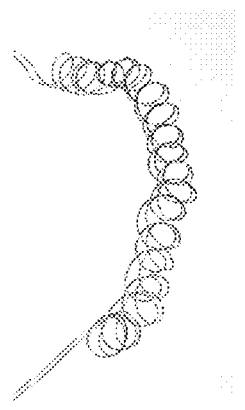
Figure 12:
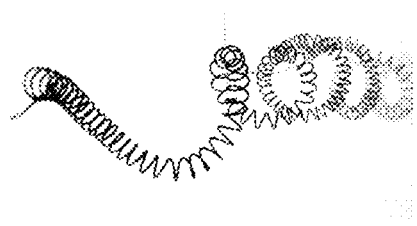
Figure 9:
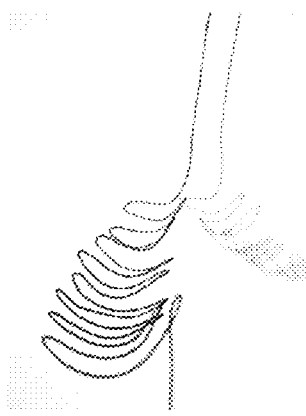
Figure 11:
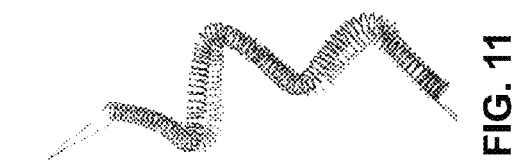
Figure 8:
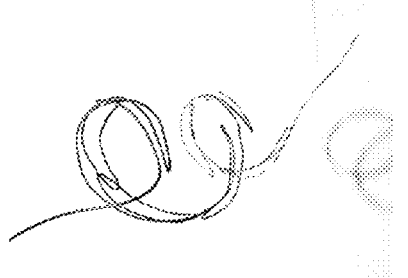

In FIG. 2, the electrode lead is shown upon completion of the implantation. In addition to the features stated in FIG. 1, a deformable supply lead section 260 of the electrode lead is now shown. In this embodiment, the deformable supply lead section forms a coil in the distal region of the electrode lead having a diameter of 3-15 mm. The altered shape of the deformable supply lead section 260 is induced either by way of a preformation of a jacket of the supply lead and/or an electric conductor of the supply lead, or by way of a shape memory material (polymer or metal) which achieves the altered shape by way of body heat or an additional energy input (heat, light).

The helical spiral can be created by coiling the entire electrode lead, including the supply lead section located therein, or a spiral of the supply lead preferably forms inside the outer sleeve of the electrode lead, wherein the outer sleeve 270 then expands in the shape of a balloon. The latter is indicated in FIG. 2.

The inductance of the helical spiral formed by the deformable supply lead section is approximately 1 µH in the example shown, i.e. the helix comprises approximately 30 turns along a length of 10 cm, with a diameter of 1.2 cm. Together with the tissue impedance, a voltage divider therefore results which reduces the electrode heating at least by a factor of 2. Other numbers of turns may be utilized in other embodiments, e.g., 15 or any other value for example.

The electrode lead formed in this manner is MRT-suitable and does not deviate from conventional electrode leads at quality-relevant joints. Likewise, no additional electronic components are required in the electrode.

Embodiments of the altered shape of the supply lead section after implantation:

The curling (compression, accommodating a greater length in a small space) takes place during or after implantation. For example, the deformable supply lead section assumes a preformed/pre-impressed shape when a mandrel is removed. Alternatively or in addition, this takes place via the effect of heat (memory shape), i.e. due to the body's natural heat or by heating the mandrel.

The curling preferably forms in the distal region, optionally also in the proximal region or only in the proximal region.

In a further embodiment, a plurality of curled regions is formed along the electrode lead. They are preferably adapted to the local anatomical details, e.g. one shape in the upper hollow vein, a second shape in the atrium, and a third shape in the ventricle.

The altered shape can have various appearances:

These shapes are based substantially on two basic shapes and, building thereupon (by way of combination/nesting), a variety of further shapes results, as depicted in FIGS. 3 to 12.

The basic shapes are, primarily:
Helix, see FIG. 3, and
Meander, see FIG. 4.
Variants of the meander and the helix are depicted in FIGS. 5 to 12, i.e.:
Meander as torus, see FIG. 6;
Helix as torus, see FIG. 7;
Meander as helix, see FIG. 8;
Meander, shaped, see FIG. 9;
Helix, pressed flat, see FIG. 10;
Helix as meander, see FIG. 11;
Helix as helix, see FIG. 12.

The electrode leads for these curled embodiments preferably have a thickness of less than 5 F.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable elongated electrode lead comprising:
   an electrode body;
   at least one electrode pole connected to the electrode body;
   a connector; and,
   an electric supply lead which is electrically connected to the at least one electrode pole and extends from the at least one electrode pole to the connector at a proximal end of the implantable elongated electrode lead;
      wherein the electric supply lead comprises at least one deformable supply lead section, wherein said at least one deformable supply lead section is configured to assume at least one altered shape after implantation of the implantable elongated electrode lead; and,
      wherein said at least one altered shape is configured to provide an inductance that is higher in the at least one deformable supply lead section after deformation into said at least one altered shape than before deformation, wherein the inductance is at least 0.1 µH;
   an outer sleeve within which the electric supply lead is disposed;
      wherein the electric supply lead is disposed inside the outer sleeve such that the electric supply lead, in the at least one deformable supply lead section thereof, is deformable relative to the outer sleeve and inside the outer sleeve; and,
      wherein the outer sleeve is expandable in a region of the at least one deformable supply lead section, and wherein the at least one deformable supply lead section and outer sleeve are configured such that the outer sleeve expands radially in all directions in the shape of a balloon upon deformation of the at least one deformable supply lead section.

2. The implantable elongated electrode lead according to claim 1, wherein the at least one altered shape further comprises a helix.

3. The implantable elongated electrode lead according to claim 2, wherein the helix comprises at least 15 turns.

4. The implantable elongated electrode lead according to claim 2, wherein individual turns of the helix are separated from one another.

5. The implantable elongated electrode lead according to claim 1, wherein each of the at least one altered shape is pre-impressed upon the electric supply lead.

6. The implantable elongated electrode lead according to claim 5, wherein the electrical supply lead comprises a shape memory metal configured to assume the at least one altered shape after a trigger temperature is exceeded.

7. The implantable elongated electrode lead according to claim 5, wherein the implantable elongated electrode lead is configured in a preformed shape and, upon implantation, is configured to be elastically preloaded using an insertion aid that is stiffer and removable so that the electric supply lead assumes the at least one altered shape after removal of the insertion aid on the preload.

8. The implantable elongated electrode lead according to claim 7, wherein the insertion aid is a sleeve catheter or a stylet.

9. The implantable elongated electrode lead according to claim 8, wherein the electric supply lead further comprises an electric conductor which is enclosed by a jacket at least in the region of the at least one deformable supply lead section, upon which the at least one altered shape of the supply lead is pre-impressed.

10. The implantable elongated electrode lead according to claim 9, wherein the jacket is formed of a shape memory material.

11. The implantable elongated electrode lead according to claim 9, wherein the jacket is formed of an insulating plastic.

12. The implantable elongated electrode lead according to claim 5, wherein said at least one altered shape pre-impressed upon the electric supply lead comprises a plurality of curled regions pre-impressed upon and along the electric supply lead, such that the plurality of curled regions are configured to adapt to local anatomical shapes when implanted and comprise at least a first shape of a hollow upper vein of a heart, a second shape of an atrium of the heart, and a third shape of a ventricle of the heart.

13. The implantable elongated electrode lead according to claim 1, wherein the at least one deformable supply lead section has a diameter, after deformation, of more than 8 mm.

14. An implantable elongated electrode lead comprising:
   an electrode body;
   at least one electrode pole connected to the electrode body;
   a connector; and,
   an electric supply lead which is electrically connected to the at least one electrode pole and extends from the at least one electrode pole to the connector at a proximal end of the implantable elongated electrode lead;
      wherein the electric supply lead comprises at least one deformable supply lead section, wherein said at least one deformable supply lead section is configured to assume at least one altered shape after implantation of the implantable elongated electrode lead;
      wherein each of said at least one altered shape is pre-impressed upon the electric supply lead; and,
      wherein said at least one altered shape is configured to provide an inductance that is higher in the at least one deformable supply lead section after deformation into said at least one altered shape than before deformation, wherein the inductance is at least 0.1 µH;
   an outer sleeve within which the electric supply lead is disposed;
      wherein the electric supply lead is disposed inside the outer sleeve such that the electric supply lead, in the at least one deformable supply lead section thereof, is deformable relative to the outer sleeve and inside the outer sleeve; and,
      wherein the outer sleeve is expandable in a region of the at least one deformable supply lead section, and wherein the at least one deformable supply lead section and outer sleeve are configured such that the outer sleeve expands radially in all directions in the shape of a balloon upon deformation of the at least one deformable supply lead section; and,
   wherein the electric supply lead further comprises an electric conductor which is enclosed by a jacket at least in the region of the at least one deformable supply lead section, upon which the at least one altered shape of the supply lead is pre-impressed.

15. An implantable elongated electrode lead comprising:
   an electrode body;
   at least one electrode pole connected to the electrode body;
   a connector; and,
   an electric supply lead which is electrically connected to the at least one electrode pole and extends from the at least one electrode pole to the connector at a proximal end of the implantable elongated electrode lead;
      wherein the electric supply lead comprises at least one deformable supply lead section, wherein said at least one deformable supply lead section is configured to assume at least one altered shape after implantation of the implantable elongated electrode lead;

wherein each of said at least one altered shape is pre-impressed upon the electric supply lead; and, wherein said at least one altered shape is configured to provide an inductance that is higher in the at least one deformable supply lead section after deformation into said at least one altered shape than before deformation, wherein the inductance is at least 0.1 µH;

an outer sleeve within which the electric supply lead is disposed;

wherein the electric supply lead is disposed inside the outer sleeve such that the electric supply lead, in the at least one deformable supply lead section thereof, is deformable relative to the outer sleeve and inside the outer sleeve; and, wherein the outer sleeve is expandable in a region of the at least one deformable supply lead section, and wherein the at least one deformable supply lead section and outer sleeve are configured such that the outer sleeve expands radially in all directions in the shape of a balloon upon deformation of the at least one deformable supply lead section;

wherein the electric supply lead further comprises an electric conductor which is enclosed by a jacket at least in the region of the at least one deformable supply lead section, upon which the at least one altered shape of the supply lead is pre-impressed; and, wherein said at least one altered shape pre-impressed upon the electric supply lead comprises a plurality of curled regions pre-impressed upon and along the electric supply lead, such that the plurality of curled regions are configured to adapt to local anatomical shapes when implanted and comprise at least a first shape of a hollow upper vein of a heart, a second shape of an atrium of the heart, and a third shape of a ventricle of the heart.

* * * * *